US008529472B2

(12) United States Patent
Matsumura et al.

(10) Patent No.: US 8,529,472 B2
(45) Date of Patent: Sep. 10, 2013

(54) BLOOD ANALYSIS DEVICE AND BLOOD ANALYSIS SYSTEM USING THE SAME

(75) Inventors: Keisuke Matsumura, Ehime (JP); Masaki Fujiwara, Ehime (JP)

(73) Assignee: Panasonic Corporation, Osaka (JP)

( * ) Notice: Subject to any disclaimer, the term of this patent is extended or adjusted under 35 U.S.C. 154(b) by 157 days.

(21) Appl. No.: 12/675,994

(22) PCT Filed: Sep. 4, 2008

(86) PCT No.: PCT/JP2008/002449
§ 371 (c)(1),
(2), (4) Date: Mar. 2, 2010

(87) PCT Pub. No.: WO2009/031313
PCT Pub. Date: Mar. 12, 2009

(65) Prior Publication Data
US 2010/0191148 A1    Jul. 29, 2010

(30) Foreign Application Priority Data

Sep. 4, 2007   (JP) ................................. 2007-228530

(51) Int. Cl.
*A61B 5/00* (2006.01)
*B65D 81/00* (2006.01)

(52) U.S. Cl.
USPC ......................................... 600/584; 600/583

(58) Field of Classification Search
USPC ................................................ 600/583, 584
See application file for complete search history.

(56) References Cited

U.S. PATENT DOCUMENTS

| 4,323,536 | A | * | 4/1982 | Columbus ..................... 422/412 |
| 4,849,340 | A | * | 7/1989 | Oberhardt ........................ 435/13 |
| 5,208,163 | A | * | 5/1993 | Charlton et al. ................ 436/63 |
| 5,554,153 | A | * | 9/1996 | Costello et al. ..................... 606/9 |
| 5,792,944 | A | | 8/1998 | Lennert et al. |
| 5,839,446 | A | * | 11/1998 | Waner et al. ................... 128/898 |
| 5,886,252 | A | | 3/1999 | Lennert et al. |
| 5,908,416 | A | * | 6/1999 | Costello et al. ..................... 606/9 |
| 5,947,957 | A | * | 9/1999 | Morris ............................. 606/13 |
| 5,993,439 | A | | 11/1999 | Costello et al. |

(Continued)

FOREIGN PATENT DOCUMENTS

| JP | 7-55801 | 3/1995 |
| JP | 07-55801 | 3/1995 |

(Continued)

OTHER PUBLICATIONS

Japan Office action, mail date is Oct. 4, 2011.

*Primary Examiner* — Max Hindenburg
*Assistant Examiner* — Adam Eiseman
(74) *Attorney, Agent, or Firm* — Greenblum & Bernstein, P.L.C.

(57) ABSTRACT

A blood analysis device wherein a carrying part blood attached thereto can be localized to thereby facilitate handling after using. When incorporating blood collected from the punctured skin, the blood is held in a skin-puncturing device or the like so that an uncontaminated holding area can be enlarged and the degree of freedom in handling can be increased. A blood analysis device which comprises a plate type device body having a blood collection port for incorporating blood and a ventilation hole formed at a certain distance apart in a face and a passage located inside for connecting the blood collection port to the ventilation hole, and a blood analysis section located within the passage for analyzing the blood having been incorporated via the blood collection port.

4 Claims, 11 Drawing Sheets

(56) References Cited

U.S. PATENT DOCUMENTS

| | | | |
|---|---|---|---|
| 6,074,383 A * | 6/2000 | Grippi et al. | 606/14 |
| 6,165,795 A * | 12/2000 | Mize et al. | 436/69 |
| 6,521,182 B1 * | 2/2003 | Shartle et al. | 422/417 |
| 6,733,493 B2 * | 5/2004 | Gruzdev et al. | 606/9 |
| 2002/0082522 A1 * | 6/2002 | Douglas et al. | 600/583 |
| 2004/0171968 A1 * | 9/2004 | Katsuki et al. | 600/583 |
| 2005/0245844 A1 * | 11/2005 | Mace et al. | 600/583 |
| 2006/0147343 A1 | 7/2006 | Teramoto | |
| 2009/0281455 A1 | 11/2009 | Fujiwara et al. | |
| 2009/0318790 A1 | 12/2009 | Fujiwara et al. | |
| 2009/0318834 A1 * | 12/2009 | Fujiwara et al. | 600/583 |
| 2010/0030037 A1 | 2/2010 | Matsumoto et al. | |
| 2010/0042016 A1 | 2/2010 | Akiyama | |
| 2010/0068795 A1 | 3/2010 | Shinohara et al. | |
| 2010/0234768 A1 * | 9/2010 | Uchiyama et al. | 600/583 |
| 2010/0292608 A1 | 11/2010 | Doi | |

FOREIGN PATENT DOCUMENTS

| | | |
|---|---|---|
| JP | 9-502119 | 3/1997 |
| JP | 09-502119 | 3/1997 |
| JP | 3342477 | 8/2002 |
| JP | 2003-265444 | 9/2003 |
| WO | 99/30152 | 6/1999 |
| WO | 2004/113927 | 12/2004 |
| WO | 2006/093206 | 9/2006 |
| WO | 2007/091671 | 8/2007 |
| WO | 2007/108519 | 9/2007 |
| WO | 2008/136473 | 11/2008 |

* cited by examiner

BLOOD ANALYSIS DEVICE AND BLOOD ANALYSIS SYSTEM USING THE SAME

TECHNICAL FIELD

The present invention relates to a blood analysis device that analyzes, for example, blood sugar levels, lactic acid levels or cholesterol levels, and a blood analysis apparatus using the blood analysis device.

BACKGROUND ART

Diabetes patients need to measure their blood sugar level (glucose level) on a regular basis and inject insulin based on the measured blood sugar level to maintain a normal blood sugar level. To maintain this normal blood sugar level, diabetes patients need to measure the blood sugar level on a regular basis. Therefore, patients puncture the skin of their fingers and so forth by using a puncturing apparatus, sample a small amount of blood exuding from the skin and make this sampled blood contact a blood analysis device to take the blood into the blood analysis device. When blood is taken into the blood analysis device, its components such as blood sugar levels are analyzed by a analysis section of the blood test apparatus.

Conventionally, the test strip disclosed in Patent Document 1, for example, has been known as a blood analysis device used to analyze the sampled blood. This test strip has an elongated plate shape, and its base end is connected to a blood component measuring apparatus to take in blood from an opening of a spot application section formed on a leading end surface. In addition, the test strip has a capillary reaction chamber (capillary) that is formed inside and connects to the opening at the leading end, and has a ventilation hole in communication with the capillary reaction chamber provided in a concave part formed on a side end surface so as not to block the flow of blood introduced in this capillary reaction chamber. By this configuration, blood spotted at the spot application section is taken inside from the opening and reaches the capillary reaction chamber, and then, the reaction in the capillary reaction chamber is detected in the blood component measuring apparatus through electrodes to analyze the blood.

Patent Document 1: Japanese Patent No. 3342477

DISCLOSURE OF INVENTION

Problems to be Solved by the Invention

However, when such a conventional blood analysis device takes blood inside, the surround of the spot application section that takes in blood might be stained with blood and also blood might flow out from the ventilation hole. For this reason, there has been such a problem that the user is stained with blood when removing the blood analysis device from the blood component measuring apparatus after the blood analysis device is used, and therefore it is inconvenient for the user.

Particularly, assuming that an apparatus that has a puncturing device and a blood analysis device and automatically performs a series of puncturing and analysis operations, the blood analysis device is automatically inserted in and ejected from the apparatus, so that parts of the apparatus in contact with the blood analysis device increases. By this means, with conventional blood analysis devices, the part stained with blood may touch the apparatus body, and therefore, there has been a demand to localize the parts stained with blood and therefore the area to hold for mounting the blood analysis device is widened.

It is therefore an object of the invention is to provide a blood analysis device: that is easily handled by localizing parts stained with blood after being used; that has a wide holding area on which blood adheres even if the device is held by a puncturing device and so forth for puncturing skin and takes in the blood from the punctured skin; and that allows a high degree of freedom of use, and a blood test apparatus using this blood analysis device.

Means for Solving the Problem

In order to achieve this object, the blood analysis device according to the present invention has a configuration including: a plate-like device body that includes a blood collecting entrance for taking in blood and a ventilation hole apart from each other on one plane and open, and that has inside a passage section that communicates the blood collecting entrance with the ventilation hole; and a blood analyzing section that is provided in the passage section and that analyzes the blood taken in through the blood collecting entrance.

In addition, the blood analysis device according to the present invention has a configuration including: a casing in which a blood analysis device having the above-described configuration is mounted, which has a puncturing opening arranged facing a blood collecting entrance of the blood analysis device mounted; and a puncturing section that is arranged facing the puncturing opening in the casing, and that punctures skin located in the puncturing opening through the blood collecting entrance of the blood analysis device mounted inside.

Advantageous Effects of Invention

According to the present invention, when blood is taken in a blood analysis section through a blood collecting entrance, blood touches only one surface even if blood moves from the blood collecting entrance to the ventilation hole, and therefore the parts stained with blood can be localized. Consequently, when the blood analysis device is held by a puncturing device and so forth for puncturing skin and takes in blood from the punctured skin, the held area not stained with blood is widened, and therefore the blood analysis device to allow a high degree of freedom of use can be provided.

BEST MODE FOR CARRYING OUT THE INVENTION

Now, the embodiments of the present invention will be described in detail with reference to the drawings.

Figure 1:
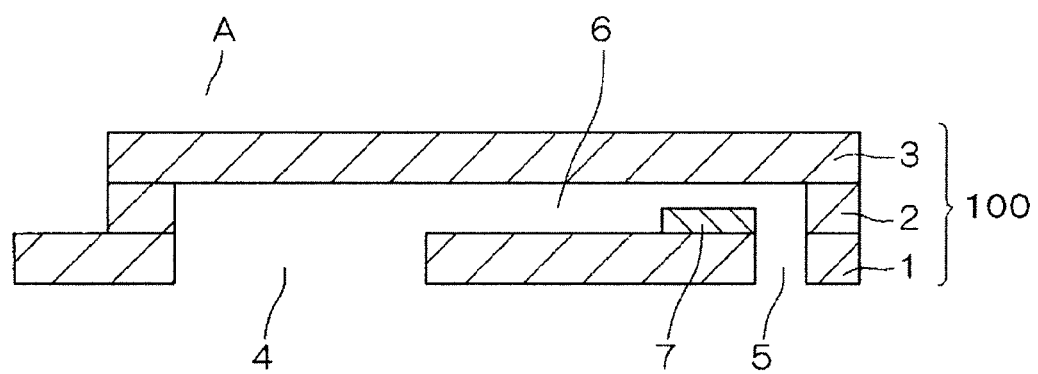
FIG. 1 is a cross sectional view showing a configuration of the primary parts of a blood analysis device according to an embodiment of the present invention.
Figure 2:
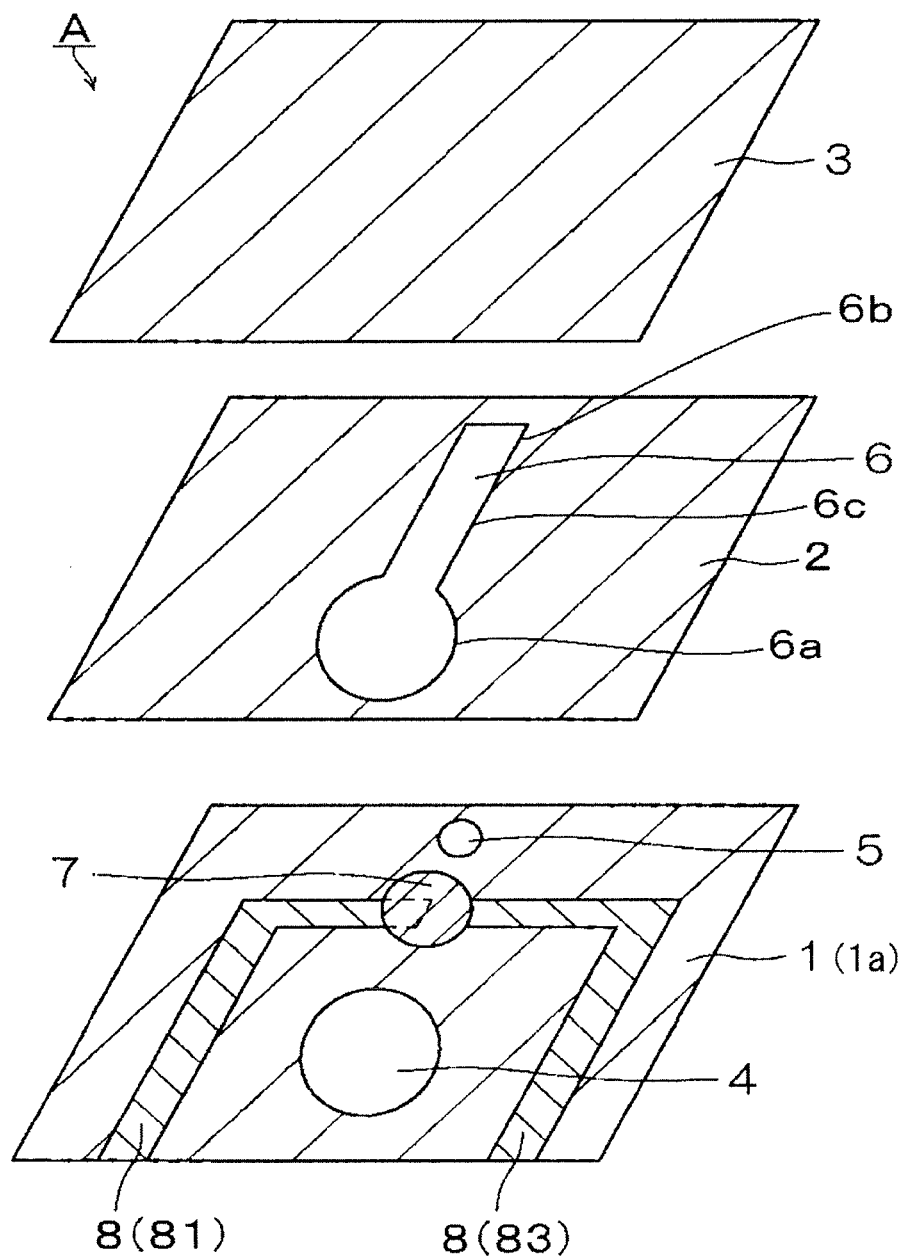
FIG. 2 is an exploded perspective view explaining a configuration of the primary parts of the blood analysis device according to the embodiment.

FIG. 1 and FIG. 2 show the primary parts of blood analysis device A according to an embodiment of the present invention. Blood analysis device A has: one surface 1a on which blood collecting entrance 4 that takes in blood and ventilation hole 5 are provided apart from one another; passage 6 that is formed inside and that places blood collecting entrance 4 in communication with ventilation hole 5; and blood analysis section 7 that is coupled with passage 6 and that analyzes the blood taken in through blood collecting entrance 4.

Figure 9:
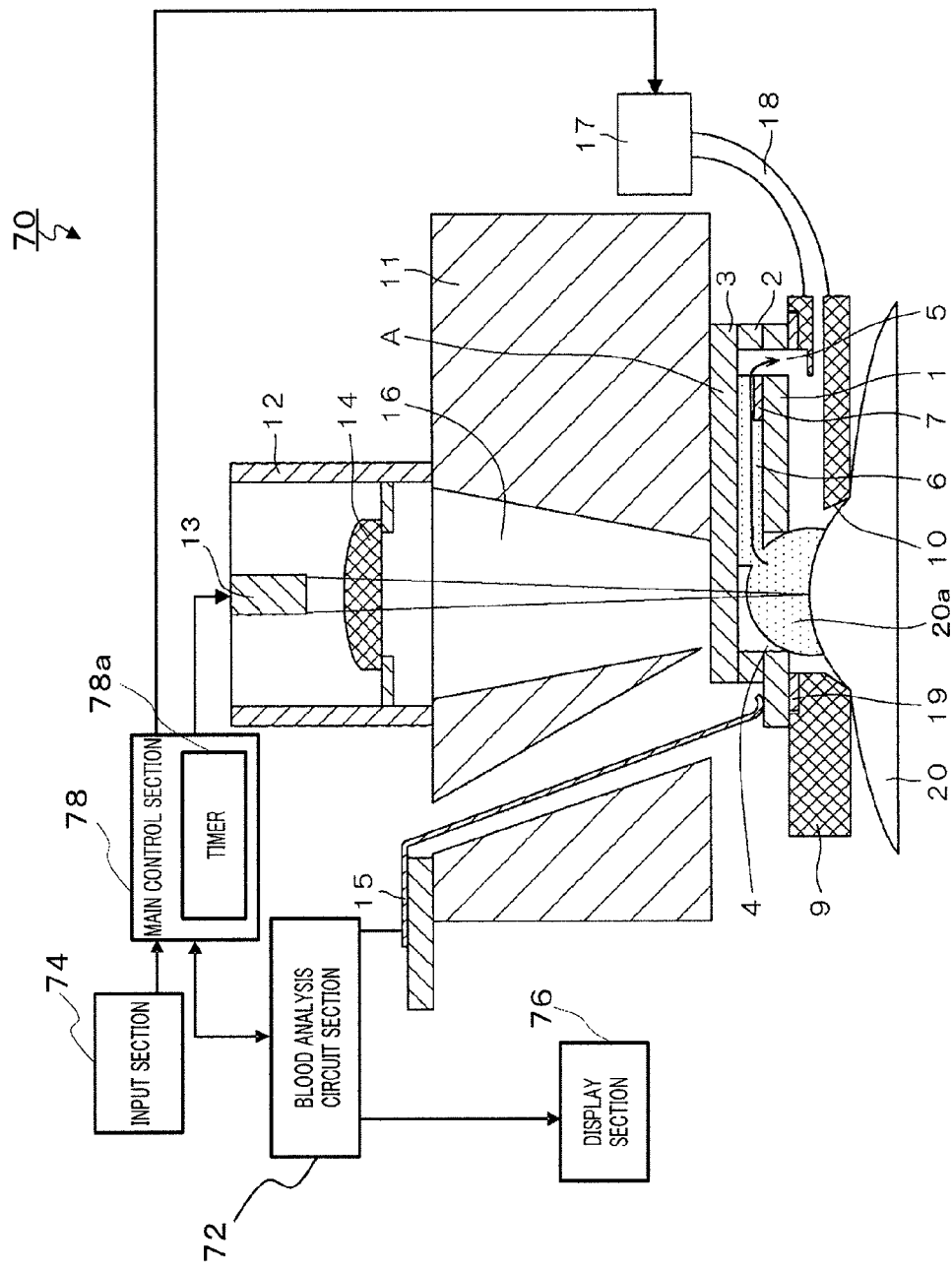
FIG. 9 is a cross sectional view of the primary parts of the blood analysis apparatus of the embodiment.

Here, blood analysis device A has device body 100 formed of a thin plate, and is used by being removably mounted in blood analysis apparatus 70 (see FIG. 9). Here, blood analysis device A has electrodes connected to a plurality of connectors provided in blood analysis apparatus 70 when blood analysis device A is mounted in blood analysis apparatus 70.

In device body 100, blood collecting entrance 4 is open to the side in which blood analysis device A is placed on the skin and forms, together with one end part 6a of passage 6, a storing section for storing blood. Here, this blood collecting entrance 4 is preferably formed around the center of device body 100.

Since blood collecting entrance 4 is coupled with passage 6 through one end part 6a of passage 6, blood stored in the storing section through blood collecting entrance 4 flows in passage 6 by capillary action and reaches blood analysis section 7 provided in passage 6. The other end part 6b of passage 6 is coupled with ventilation hole 5 that is open on one surface (under surface) 1a in the same plane as blood collecting entrance 4.

Device body 100 is configured by stacking a first plate-like body (base member), a second plate-like body (spacer member) and a third plate-like body (cover member), which have approximately the same outer shape. Here, blood analysis device A is formed by stacking spacer member 2 and cover member 3 in order on the other surface (upper surface) side of base member 1, which is a base plate, pasting spacer member 2 on the other surface (upper surface) of base member 1 and pasting cover member 3 on the upper surface of this spacer member 2.

In device body 100, wiring 8 that is located in a position in passage 6 before ventilation hole 5 and is connected to blood analysis section 7 on which a reagent is placed is provided in base member 1. Wiring 8 is provided in base section 1 to extend from blood analysis section 7 toward the end opposite ventilation hole 5.

Both extended ends of wiring 8 are not covered with spacer member 2 as evidenced by FIG. 2, and therefore both ends of wiring 8 are exposed toward the upper surface side.

With blood analysis device A, the thickness of spacer member 2 is set in the range of 0.01 to 0.5 mm in order to generate capillary action in passage 6 in device body 10, and preferably, the thickness is 0.1 mm.

In addition, here, preferably, the thickness of base member 1 is approximately the same as or greater than the thickness of spacer member 2 in order to adjust the capacity of the storing section and the capacity of passage 6 in device body 100. For example, preferably, the thickness is set as "the thickness of base member 1: the thickness of spacer member 2=1:1 to 5:1". More preferably, "the thickness of base member 1: the thickness of spacer member 2=2:1". In addition, preferably, the thickness of cover member 3 is less than that of base member 1, and therefore device body 100, that is, blood analysis device A itself is thinned. For example, preferably, "the thickness of base member 1: the thickness of spacer member 2: the thickness of cover member 3=2:1:1" and so forth. Moreover, for example, the outer shape of base member 1 is a rectangle of about 12 mm×15 mm in a plane view, in order to make the outer shape of device body 100 be a rectangle of about 12 mm×15 mm in a plane view.

Figure 3:
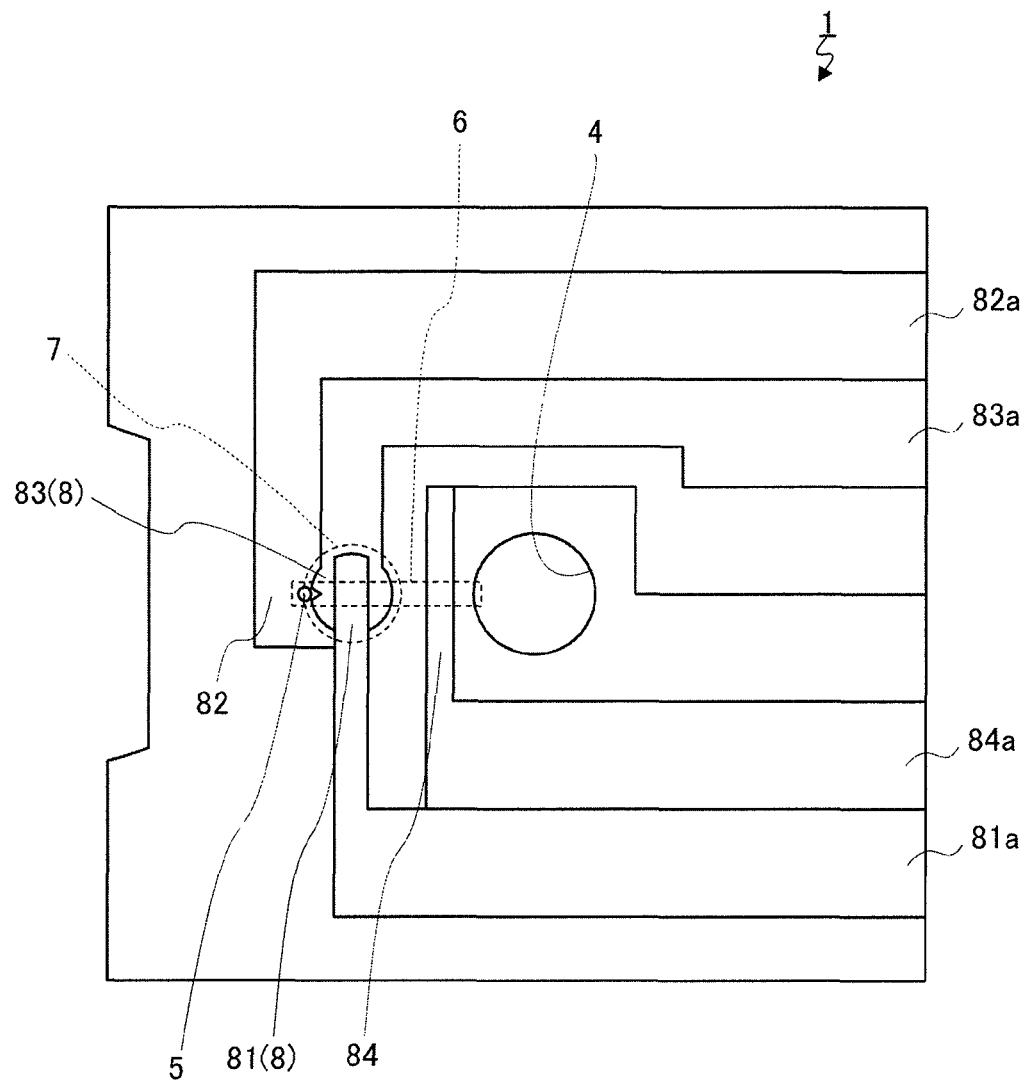
FIG. 3 is a perspective plane view showing a base member of the blood analysis device of the embodiment.
Figure 4:
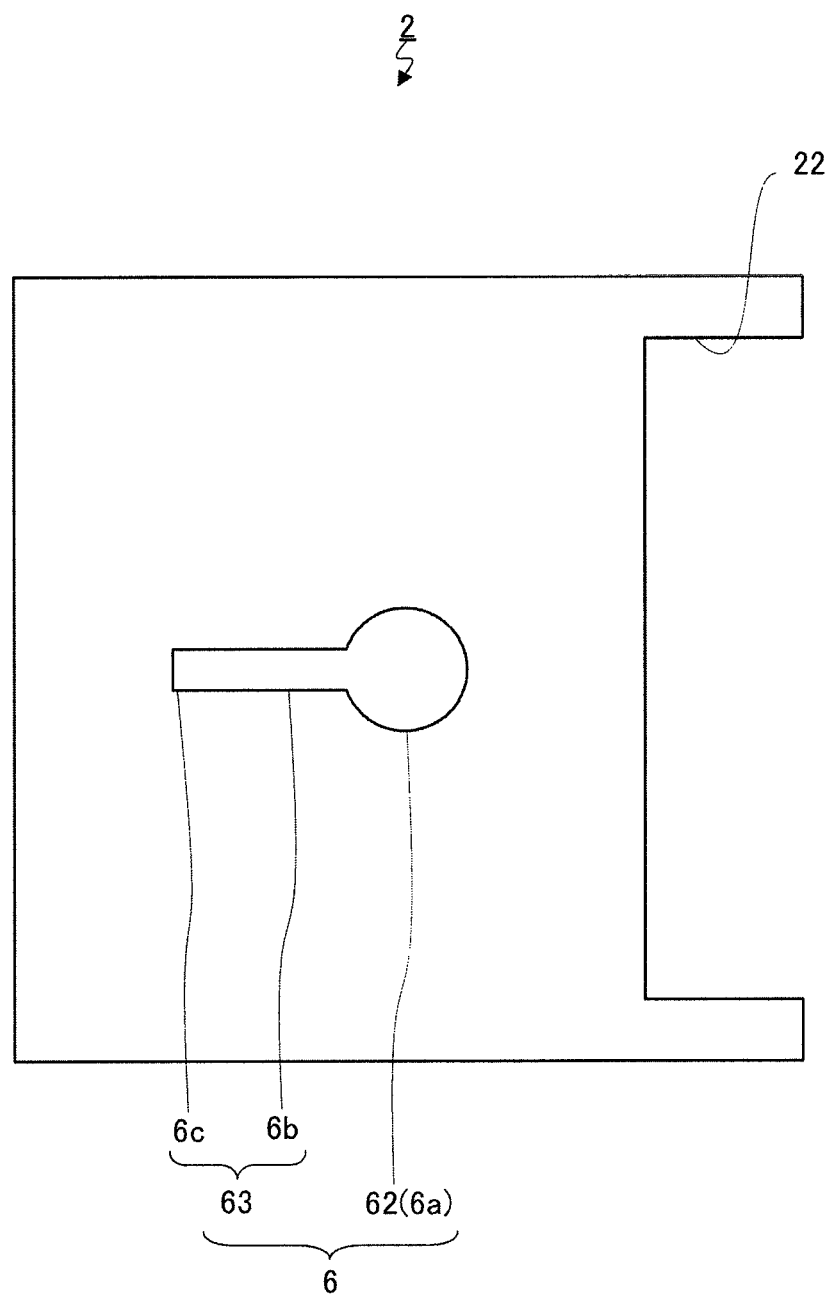
FIG. 4 is a perspective plane view showing a spacer member of the blood analysis device of the embodiment.
Figure 5:
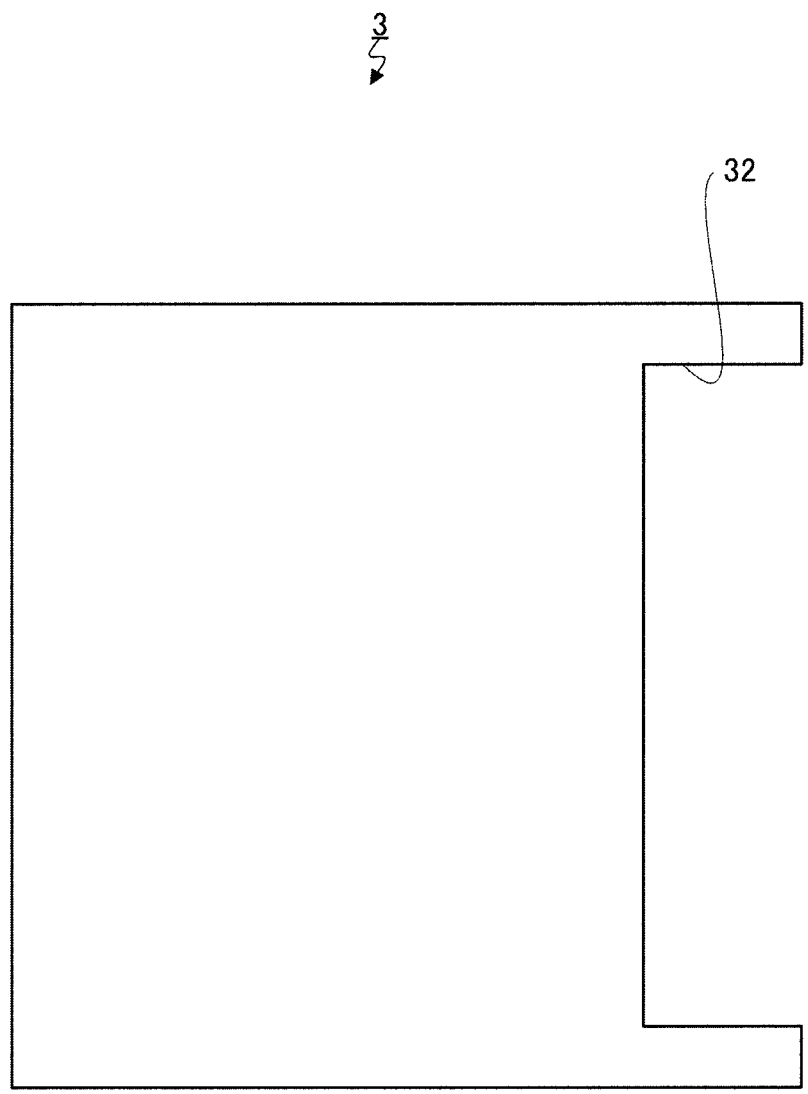
FIG. 5 is a perspective plane view showing a cover member of the blood analysis device of the embodiment.

FIG. 3 to FIG. 5 are drawings explaining base member 1, spacer member 2 and cover member 3 constituting blood analysis device A according to an embodiment of the present invention. FIG. 3 is a perspective plane view showing base member 1 of blood analysis device A; FIG. 4 is a perspective plane view showing spacer member 2 of blood analysis device A; and FIG. 5 is a perspective plane view showing cover member 3 of blood analysis device A.

In base member 1 shown in FIG. 3, blood collecting entrance 4 and ventilation hole 5 are formed in positions apart from one another to penetrate the upper surface and the under surface, respectively. Here, blood collecting entrance 4 and ventilation hole 5 are formed in blood analysis apparatus 70 (see FIG. 9) that analyzes components of blood using blood analysis device A, so as to be arranged linearly along the direction to pull out from blood analysis apparatus 70. Here, with respect to blood collecting entrance 4, ventilation hole 5 is arranged in the side opposite the position in which connection electrodes (both ends of wiring 8) connected to blood analysis apparatus 70 are arranged.

Base material of base member 1 is made of insulating material, and here, the base material is made of PET (Polyethylene Terephthalate).

In base member 1, blood collecting entrance 4 is formed in a position overlapping the skin to be punctured, that is, the puncturing position.

Here, preferably, blood collecting entrance 4 is formed to have a diameter in the range of 0.5 mm to 5.0 mm, and more preferably, a diameter is in the range of 1.0 mm to 3.0 mm. Here, blood collecting entrance 4 is formed to have a diameter of 2.0 mm.

Ventilation hole 5 is formed in base member 1 to place apart from the puncturing position in which blood collecting entrance 4 is located. In other words, ventilation hole 5 is located in base member 1, in a position apart from the puncturing position in which the finger is placed. By this means, ventilation hole 5 is not closed by the finger placed on the puncturing position when puncturing is performed.

If the diameter of ventilation hole 5 is too small, the air resistance increases in passage 6 coupled with ventilation hole 5. By this means, the speed of introduction of blood in passage 6 slows down and passage 6 is easily clogged with dust and so forth. Meanwhile, ventilation hole 5 formed in base member 1 is too large, the blood easily overflows when being taken in passage 6 through blood collecting entrance 4.

By this means, circular ventilation hole 5 in the present embodiment is preferably formed in base member 1 as a hole having a diameter of 0.05 mm to 2.0 mm, and more preferably, formed in base member 1 as a hole having a diameter of 0.1 mm to 1.0 mm.

Although ventilation hole 5 of the present embodiment has a circular shape, the shape is not limited to this and ventilation hole 5 may be formed of any shape such as an elongated hole in base member 1. For example, as shown in FIG. 6, cross-shaped ventilation hole 51, triangular ventilation hole 52 or quadrangular ventilation hole 53 may be formed in base member 1.

Figure 6A:
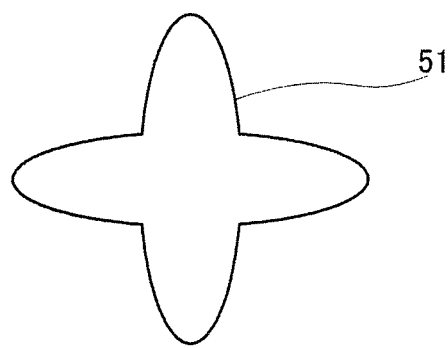
FIG. 6 is a drawing showing an alternative example of a ventilation hole of the blood analysis device of the embodiment.
Figure 6B:
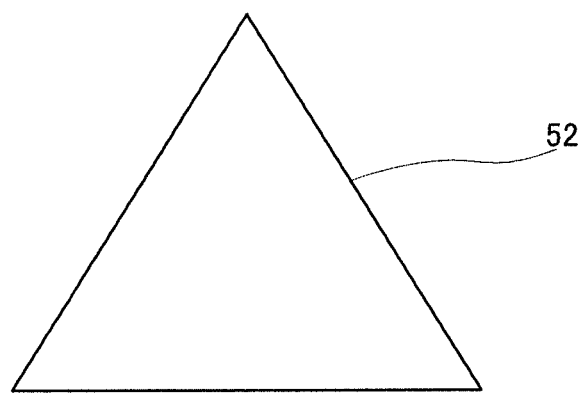
Figure 6C:
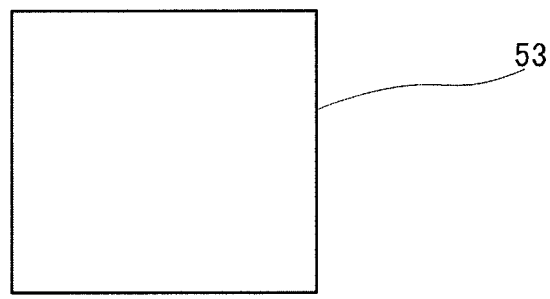

As shown in FIG. 6A, FIG. 6B and FIG. 6C, if the shape of ventilation hole 5 is a cross (ventilation hole 51), a triangle (ventilation hole 52) and a quadrangle (ventilation hole 53), all ventilation holes 51, 52 and 53 are not easily closed even if the finger touches ventilation holes 51, 52 and 53.

In addition, if an ventilation hole is formed by a plurality of straight lines as ventilation holes 51, 52 and 53, a film of blood that covers ventilation holes 51, 52 and 53 is not easily formed when liquid such as blood is adhered on ventilation holes 51, 52 and 53. By this means, ventilation holes 51, 52 and 53 themselves are prevented from being closing. Here, if ventilation hole 5 is formed by punching out base member 1, the number of steps of processing does not differ as a result of difference of shape.

Moreover, detection electrodes 81 to 84 including wiring 8 and connection electrodes 81a, 82a, 83a and 84a, connected to detection electrodes 81 to 84, respectively, are provided on the upper surface of base member 1, that is, the surface on which spacer member 2 is stacked. Here, wiring 8, which is schematically shown in FIG. 2, corresponds to detection electrodes 81 and 83, and connection electrodes 81a and 83a.

Detection electrodes 81 to 84 and connection electrodes 81a, 82a, 83a and 84a are formed by forming a conductive layer by the sputtering method or the vapor deposition method using materials such as gold, platinum, or palladium and by applying Nd: YAG laser (wavelength: 1064 nm) machining. Here, detection electrodes 81 to 84 and connection electrodes 81a, 82a, 83a and 84a constitute the main body of base member 10 by depositing platinum on the base material made of PET.

In the opening (through-hole 62 and slit 63) of spacer member 2 overlapping base member 1, the ends of detection electrodes 81 and 83, which are arranged near blood collecting entrance 4 but not near ventilation hole 5, are reaction parts. By applying the reagent on the reaction parts, a reagent layer is formed, and this reagent layer and the reaction parts constitute blood analysis section 7. When blood passes through passage 6 and reaches blood analysis section 7, the components of blood are analyzed through detection electrodes 81 to 84. Here, the reagent layer can be obtained by adding and dissolving PQQ-GDH (0.1 to 5.0 U/sensor), potassium ferricyanide (10 to 200 millimoles), maltitol (1 to 50 millimoles) and taurine (20 to 200 millimoles) in a CMC solution of 0.01 to 2.0 wt % to prepare a reagent solution, by dropping the reagent solution on detection electrodes 171 and 173 (see FIG. 22) formed on substrate 161 and drying. This reagent layer reacts with blood, and a signal resulting from the reaction is outputted to the apparatus body of blood analysis circuit section 72 (see FIG. 7) through wiring 8 and measured.

The under surface of base member 1 is a surface on which the blood is spotted, and here, the under surface is coated with water repellent finish. This water repellent finish prevents the blood applied in the vicinity of blood collecting entrance 4 from flowing to ventilation hole 5, in the under surface of base member 1.

To produce base member 1, first, Pd is applied on an insulating substrate as a base material made of PET by the sputter deposition method, and then, a slit is provided using a Nd: YAG laser to form an electrode pattern of detection electrodes 81 to 84, connection electrodes 81a, 82a, 83a and 84a and so forth. Next, the reagent is dropped on the predetermined portions (reaction parts of detection electrodes 81 and 83) of the formed electrode patterns and dried to form a reagent layer. After that, the insulating substrate is processed by press working, blade machining, and CO2 laser (wavelength: 930 nm) machining to form blood collecting entrance 4 and ventilation hole 5. With the present embodiment, blood collecting entrance 4 is formed by press working or blade machining, and ventilation hole 5 is formed by CO2 laser machining. Here, The processing order to process base member 1 is not limited and the processing may be performed as follows: hole machining by press working or blade machining, sputter deposition, Nd: YAG laser machining and reagent application may be performed in the described order; sputter deposition, Nd: YAG laser machining, hole machining by press working or blade machining and reagent application may be performed in the described order; or sputter deposition, hole machining by press working or blade machining and Nd: YAG laser machining may be performed in the described order.

Here, preferably, the blood collecting entrance is formed by Nd: YAG laser machining after the reagent is applied. The reason is to prevent sensor response (the response of detection electrodes) from deteriorating because smoke including insulating substrate materials generated during Nd: YAG laser machining adheres on the surface of the reaction part of detection electrodes. In addition, the reason is that the surface state of a coating section forming the reagent layer deteriorate locally as a result of the smoke and deteriorates the spread of the reagent, and therefore it is possible to impair the uniformity of the reagent layer.

Spacer member 2 is stacked on the upper surface of base member 1 that is formed described above in a state in which connection electrodes 81a and 83a constituting wiring 8 and the other connection electrodes 82a and 84a are exposed.

Spacer member 2 shown in FIG. 4 has an insulating substrate made of an insulating material such as PET and adhesive layers (not shown) that are coated on both surfaces of the insulating substrate and bond base member 1 and cover member 3.

In the insulating substrate of spacer member 2, through-hole 62 formed in a predetermined position, slit-like opening (hereinafter referred to as "slit") 63 that is processed to form main body 6c of passage 6 when base member 1 and cover member 3 are pasted and cutout section 22 that makes connection electrodes 81a, 82a, 83a and 84a of base member 1 be exposed are formed.

Though-hole 62 is formed in the insulating substrate in a predetermined position overlapping blood collecting entrance 4 of base member 1, is formed on approximately the concentric circle with blood collecting entrance 4 and communicates with blood collecting entrance 4. Here, preferably, the diameter of through-hole 62 is lager than the diameter of blood collecting entrance 4 of base member 1.

Through-hole 62 forms one end 6a of passage 6, and a puncturing section (laser light) passes through through-hole 62 when the skin is punctured. Here, when the puncturing section is a needle, the needle passes through through-hole 62.

Slit 63 connecting through-hole 62, base member 1 and cover member 3 located above and below constitute a capillary (corresponding to passage body 6c of passage 6) for introducing blood by capillary action and the other end 6b of passage 6.

The other end 6b of slit 63 is located in spacer member 2 in a position overlapping ventilation hole 5 and communicates with ventilation hole 5.

Here, it is preferable that the shape of capillary (slit 63) included in spacer member 2 is formed such that the width is in the range of 0.1 mm to 3.0 mm and the total length is in the range of 1.0 mm to 3.0 mm. Here, slit 63 is formed by cutting out a part of the insulating substrate of spacer member 2 so as to make the width be 0.6 mm and make the length (from the edge of the through-hole to the other end 6b) be 2.5 mm.

Cutout section 22 is formed by cutting out the portion facing connection electrodes 81a, 82a, 83a and 84a of base member 1 and makes connection electrodes 81a, 82a, 83a and 84a contact the measuring apparatus body of the blood analysis apparatus when blood analysis device A is mounted in the blood analysis apparatus.

As the adhesive forming the adhesive layers of spacer member 2, hot-melt adhesive, adhesive paste, UV cure adhesive and so forth are taken for example. With the present embodiment, spacer member 2 is located between base member 1 and cover member 3 and pasted on both of base member 1 and cover member 3 using hot-melt adhesive.

Here, as for the thickness of each member of spacer member 2, the thickness of the insulating substrate is preferably 30 to 250 μm, and the thickness of adhesive layers is preferably 5 to 50 μm. In addition, preferably the thickness of the adhesive layer is optimized in consideration of the unevenness of the materials to be bonded. The reason is that the processing accuracy is deteriorated if the thickness increases more than necessary and the adhesive might dripping or bleeding when the members are pasted.

With the present embodiment, the capillary can be formed by pasting spacer member 2 on base member 1 such that the opening of spacer member 2 is located on blood analysis section 7, which is configured by coating, with reagent, the reaction parts having detection electrodes 81 and 83 of base member 1. By this means, the area of detection electrodes 81 and 83 reacting in blood analysis section 7 is also limited. Consequently, the optimal thickness of adhesive used for pasting is 20 to 30 μm.

As described above, the opening that defines passage 6 in device body 100 is formed in spacer member 2 by sandwiching spacer member 2 between base member 1 and cover member 3, and this opening is formed in a location overlapping with blood collecting entrance 4 of base member 1, communicates with blood collecting entrance 4 and has the through-hole constituting one end 6a of passage 6 and a slit in communication with the through-hole and extending to the ventilation hole 5 side.

Depending on the thickness (0.1 mm) of this spacer member 2, a space for the capillary (corresponding to passage 6) in blood analysis device A is set. Therefore, the shape of capillary can be adjusted by adjusting the thickness of spacer member 2.

Cover member 3 that covers from above the openings (through-hole 62 and slit 63) is provided on the upper surface of spacer member 2 configured as described above.

Cover member 3 shown in FIG. 5 has cutout section 32 that has approximately the same outer shape as spacer member 2 and that is cut out in the same shape as cutout section 22 in a location overlapping cutout section 22 of spacer member 2. By this means, in blood analysis device A, connection electrodes 81a, 82a, 83a and 84a provided on the upper surface of base member 1, which is the bottom layer of device body 100, are exposed outward through cutout sections 22 and 32 located in positions in the above surface side facing the connection electrodes.

When blood analysis device A is mounted in the blood test apparatus having a puncturing section and used, the material for cover member 3 differs between a case where a needle is used as the puncturing section for puncturing skin and a case where laser light is used as the puncturing section for puncturing skin. When blood analysis device A is used in the blood analysis apparatus using a needle as the puncturing section, the material of cover member 3 is not limited provided that the needle can be inserted through in the puncturing operation. Meanwhile, blood analysis device A is mounted in a blood analysis apparatus having the puncturing section using laser light, it is preferable that the material does not absorb within the wavelength of laser light to be used. For example, fluorine system resin is preferably used as a material to form cover member 3, and the fluorine system resin includes PTFE: Poly Tetra Fluoro Ethylene, PFA: Tetra fluoro ethylene-perfluoro alkylvinyl ether copolymer, FEP: Fluorinated Ethylene Propylene copolymer, ETFE: Ethylene Tetra Fluoro Ethylene and so forth.

Cover member 3 is made of materials allowing laser light having a wavelength of 2 to 3 μm to pass through. Here, since cover member 3 is entirely made of fluorine system resin, the entire cover member 3 allows laser light to pass through.

Here, in cover member 3, at least only the portion of blood analysis device A located in the light path of laser light, such as the portion overlapping with blood collecting entrance 4 in the depthwise direction may be made of fluorine system resin (e.g. PFA, PTFE and FEP), and cover member 3 may not be necessarily optically transparent in whole.

Here, cover member 3 is stacked on spacer member 2, which is stacked on base member 1 and therefore cover member 3 serves as a surface to form a capillary (passage body 6c of passage 6) for introducing blood. In order to limit accurately the capacity of the capillary, cover member 3 should have a flexural strength more than a certain value. Meanwhile, if the thickness of cover member 3 increases to much, it is possible to block laser light from passing through when puncturing is performed using laser light, and it is possible to block the needle from penetrating when puncturing is performed using the puncture needle. Therefore, cover member 3 should have an optimized thickness, and cover member 3 preferably has a thickness of 25 to 250 μm, and more preferably, has a thickness of 75 to 125 μm.

Figure 7:
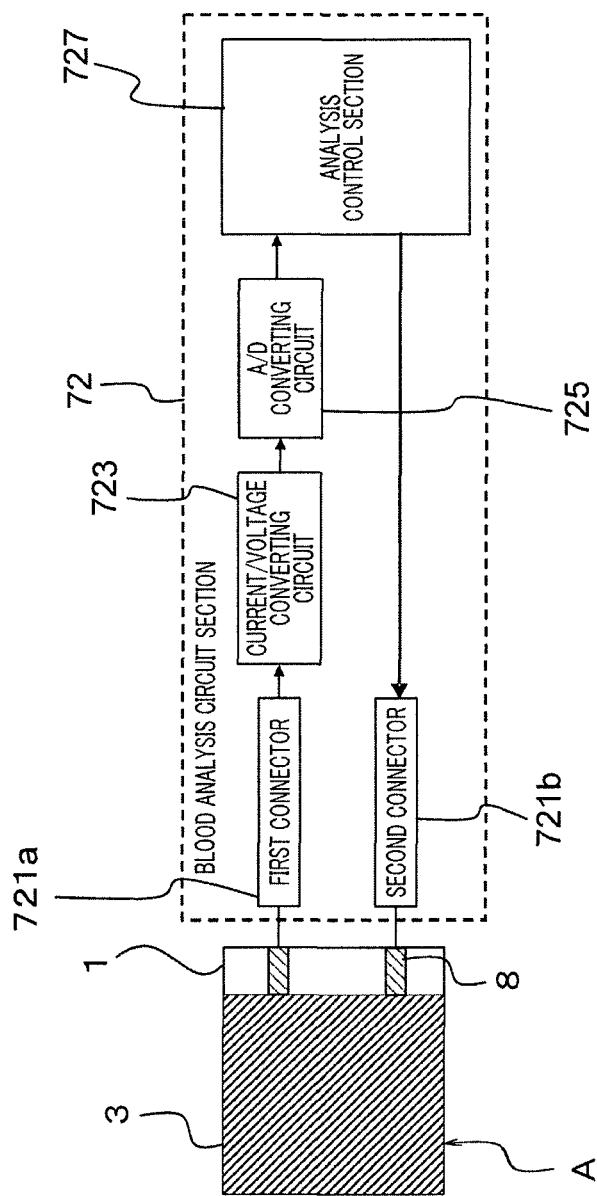
FIG. 7 is a block diagram of a blood analysis circuit section of the blood analysis device of the embodiment.

FIG. 7 is a drawing showing blood analysis device A, and a configuration of blood analysis circuit section 72 using blood analysis device A. Here, in FIG. 7, the same reference numerals as in FIG. 2 are the same or equivalent parts.

Blood analysis device A is used in a state in which blood analysis device A is connected to blood analysis circuit section 72. Blood analysis circuit section 72 is a system for measuring blood components such as blood sugar and lactic acid levels from samples such as blood supplied to blood analysis device A, which is connected to blood analysis circuit section 72.

Blood analysis circuit section 72 has first connector 721a, second connector 721b, current/voltage converting circuit 723, A/D converting circuit 725 and analysis control section 727.

First connector 721a and second connector 721b are connected to wiring 8 (connection electrodes 81 and 83) of blood analysis device A, respectively. First connector 721a is connected to current/voltage converting circuit 723. Current/voltage converting circuit 723 converts the current flowing between first connector 721a and second connector 721b to a voltage and outputs the voltage to A/D converting circuit 725.

A/D converting circuit 725 converts, to a digital value, the voltage value inputted from current/voltage converting circuit 723 connected thereto and outputs the digital value to analysis control section 727.

Analysis control section 727 outputs the desired voltage to second connector 721 connected thereto and calculates the blood components based on the digital value inputted from A/D converting circuit 725.

Now, the operations of blood analysis device A and blood analysis circuit section 72 to measure blood components of a sample by a measuring system using blood analysis device A according to the embodiment of the present invention will be described.

First, blood analysis device A is connected to first connector 721a and second connector 721b of blood analysis circuit section 72, so that analysis control section 727 outputs a certain voltage to second connector 721b. By this means, a voltage is applied between first connector 721a and second connector 721b.

The current generated between first connector 721a and second connector 721b is outputted to current/voltage converting circuit 723 and converted to a voltage. Further, the voltage converted in current/voltage converting circuit 723 is outputted to A/D converting circuit 725 and converted to a digital value by A/D converting circuit 725. The resultant digital value is outputted to analysis control section 727. Analysis control section 727 is placed in a state to always monitor the digital value inputted from A/D converting circuit 725.

In this state, when the sample is supplied to blood collecting entrance 4 (see FIG. 1 to FIG. 3) of blood analysis device A, blood is introduced into passage 6 by capillary action and reaches on blood analysis section 7. At this time, the reagent coated on blood analysis section 7 dissolves and therefore an oxidation-reduction reaction occurs, so that electrical change occurs between first connector 721a and second connector 721b.

Analysis control section 727 starts measuring blood components at the time analysis control section 727 detects that the electrical change has occurred between first connector 721a and second connector 721b as a result of changing the digital value inputted from A/D converting circuit 725, that is, that an amount of blood enough to measure has been supplied to blood analysis section 7 of blood analysis device A.

Next, analysis control section 727 controls so as not to supply a reaction voltage to second connector 721b for a certain time period and progresses the reaction of the blood with the reagent formed on blood analysis section 7. This time period is about 5 seconds. After waiting a certain time period, analysis control section 727 applies the reaction voltage to blood analysis device A through second connector 721b for a certain time period (about 5 seconds).

At the moment the application of the reaction voltage is stopped (i.e. 5 seconds have passed after starting applying the reaction voltage), a current proportional to the blood sugar level or lactic acid level of blood generates between first connector 721a and second connector 721b. This current is converted to a voltage by current/voltage converting circuit 723, and the voltage value is converted to a digital value by AD/converting circuit 725 and then outputted to analysis control section 727. Control section 727 calculates a response value using the digital value inputted from A/D converting circuit 725 and analyzes the blood.

Figure 8:
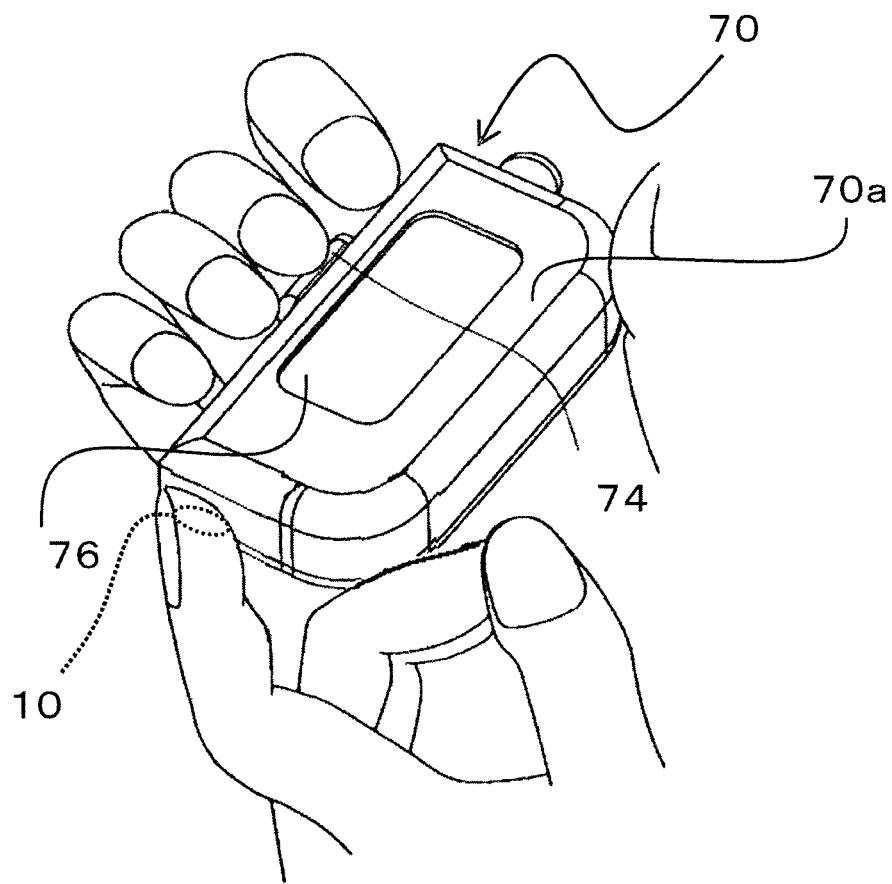
FIG. 8 is a perspective view of a blood analysis apparatus of the embodiment.

FIG. 8 is a perspective view showing the usage state of blood analysis apparatus 70 using blood analysis device A shown in FIG. 1 to FIG. 6 and blood analysis circuit section 72 shown in FIG. 7.

This blood analysis apparatus 70 is used as follows: for example, the user grips blood analysis apparatus 70 by the right hand, and pushes the tip of the index finger of the left hand onto the blood analysis apparatus (blood collecting entrance), as shown in FIG. 8.

Blood analysis apparatus 70 has casing 70a having a shape allowing the user to grip in one hand and includes input section 74 to which the user inputs to start analysis and so forth to blood analysis apparatus 70 and display device 76 for displaying the result of analysis.

FIG. 9 is a cross sectional view showing a configuration of the primary parts of blood analysis apparatus 70 shown in FIG. 8.

Blood analysis apparatus 70 has laser puncturing section 12 that punctures skin with laser light to exude blood 20a from the skin, suction pump 17, one surface (casing under side) 9 of casing 70a, on which laser light emitting opening 10 is formed, holder 11 that holds blood analysis device A and blood analysis circuit section 72.

Blood analysis apparatus 70 also has main control section 78 that is connected to laser puncturing section 12, suction pump 17, blood analysis circuit section 72, input section 74 and so forth, which constitute blood analysis apparatus 70 and that controls laser puncturing section 12, suction pump 17 and blood analysis circuit section 72 based on the signal inputted from input section 74.

In blood analysis apparatus 70, holder 11 is provided along the casing under side 9 side in casing 70a. Holder 11 holds blood analysis device A in a position in which blood collecting entrance 4 overlaps with laser light emitting opening 10. Blood analysis device A is mounted in blood analysis apparatus 70 such that blood collecting entrance 4 of base member 1 is located on the axis connecting laser light emitting opening 10 and laser puncturing section 12.

In other words, blood collecting entrance 4 of blood analysis device A removably held by holder 11 is located between holder 11 and casing under side 9, in a position above and facing laser light emitting opening 10 formed on casing under side 9 of casing 70a.

Here, ring-shaped packing section 19 is provided on the circumference of laser light emitting opening 10 of casing under side 9 so as to contact the circumference of blood collecting entrance 4 and ventilation hole 5 of base member 1.

By this means, when blood analysis device A is mounted in holder 11, packing section 19 contacts the under surface of the circumference of blood collecting entrance 4 and ventilation hole 5 of base member 1 located on casing under side 9 inside the casing, and therefore the configuration providing airtightness can be obtained.

When holding blood analysis device A, holder 11 has electrode 15 connected to connection electrodes 81a, 82a, 83a and 84a (see FIG. 3) of blood analysis device A. Blood is analyzed by blood analysis circuit section 72 of blood analysis apparatus 70 through electrode 15, and the result of the analysis is outputted to display device 76 of blood analysis apparatus 70 and then displayed on display device 76.

In addition, of holder 11 that holds blood analysis device A is provided with cone-shaped opening 16 in a portion through which laser light emitting opening 10 and laser puncturing section 12 are connected.

Holder 11 has opening 16 in a position overlapping with laser light emitting opening 10. Laser light emitting opening 10, blood collecting entrance 4 and hole 62 are located on the same axis as on this opening 16.

In the casing, laser puncturing section 12 is located in the side (upper side) opposite laser light emitting opening 10 of blood analysis device A through holder 11.

Laser puncturing section 12 is composed of laser unit section 13 that generates laser light and focusing lens 14 that focuses laser light.

Figure 10:
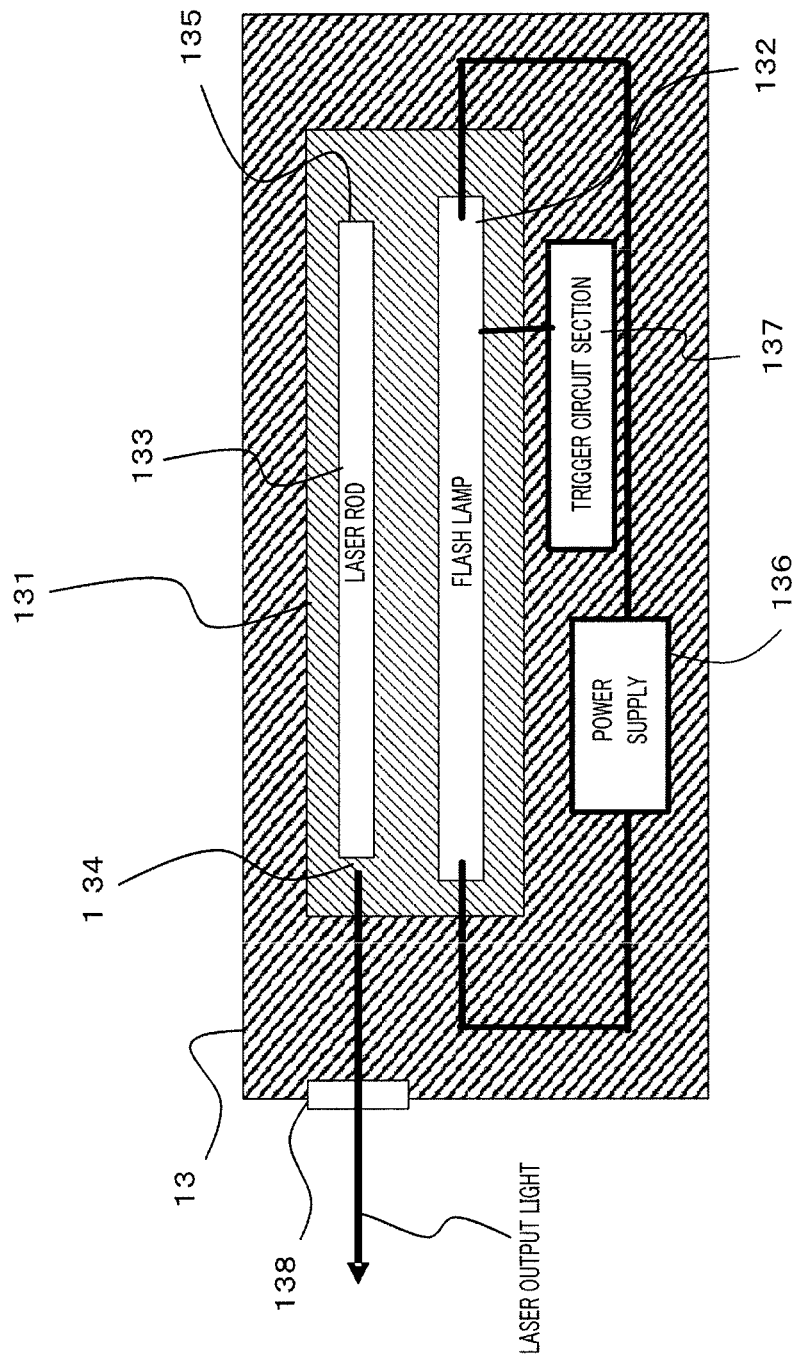
FIG. 10 is a block diagram of a laser unit section of the blood analysis apparatus of the embodiment.

FIG. 10 is a block diagram showing laser unit section 13.

In laser unit section 13 shown in FIG. 10, lens-barrel 131 has an elliptical tubular shape, and its inner circumference surface is mirror-finished in order to reflect the light source efficiently.

Here, lens-barrel 131 is formed to have an elliptical shape, flash lamp 132 (an example of light source) is disposed on one focal point of this lens-barrel 131 and laser rod 133 is disposed on the other focal point. By this means, light is emitted from flash lamp 132, and laser rod 133 is illuminated with this light efficiently.

First reflecting film 134 having a reflectivity of 85% to 95% is formed on one end surface of laser rod 133. In addition, second reflecting film 135 having a reflectivity equal to or more than 99% is formed on the other end surface of laser rod 133.

Flash lamp 132 is configured by enclosing therein xenon gas. Power supply 136 is connected to both ends of this flash lamp 132.

When trigger circuit section 137 applies a voltage of 5 to 10 kV instantaneously after power supply 136 applies, to flash lamp 132, a voltage of 200 V to 700 V from both ends of flash lamp 132, inductive discharge starts and then the current from power supply 136 flows in flash lamp 132, so that flash lamp 132 emits light. This emitted light is focused on laser rod 133 by lens-barrel 131.

As described above, the light focused on laser rod 133 excites a laser activating material (Er: YAG), which is doped and exists in laser rod 133, and generates light having a wavelength of about 2.94 μm.

The generated light resonates between first reflecting film 134 and second reflecting film 135 in laser rod 133 and is amplified.

The amplified light having an intensity higher than a certain threshold passes through first reflecting film 134, passes through exit hole 138 and is outputted outside as laser output light (laser light). Since laser rod 133 in which Er: YAG is doped is used in laser unit section 13 according to the present embodiment, laser unit section 13 emits laser light having the wavelength of about 2.94 μm.

Here, referring back to FIG. 9, and laser light is emitted from exit hole 138 (see FIG. 10) of laser puncturing section 12 above holder 11, in the axial direction of laser unit section 13, is inserted into opening 16 formed in holder 11 and passes through laser light emitting opening 10.

Suction pump 17 shown in FIG. 9 is located outside laser light emitting opening 10 formed in casing under side 9 of casing 70a (see FIG. 8) and is coupled with laser light emitting opening 10 through negative pressure path 18. Here, negative pressure path 18, coupled with suction pump 17, penetrates casing under side 9 and communicates with laser light emitting opening 10 formed in casing under side 9, and blood collecting entrance 4 and ventilation hole 5 formed on one surface 1a of blood analysis device A located in casing under side 9. When laser light emitting opening 10 is covered with finger 20 in the puncturing operation, negative pressure path 18 is coupled with a space sealed by finger 20, casing under side 9 and blood analysis device A.

Suction pump 17 applies a negative pressure to below blood analysis device A through negative pressure path 18 and allows the skin of finger 30 located below blood analysis device A to swell. By this means, blood 20a exuding from the punctured skin is taken in passage 6 of blood analysis device A and easily extends to blood analysis section 7.

Nest, the operation of blood sampling and analysis in blood analysis apparatus 70 will be described.

Figure 11:
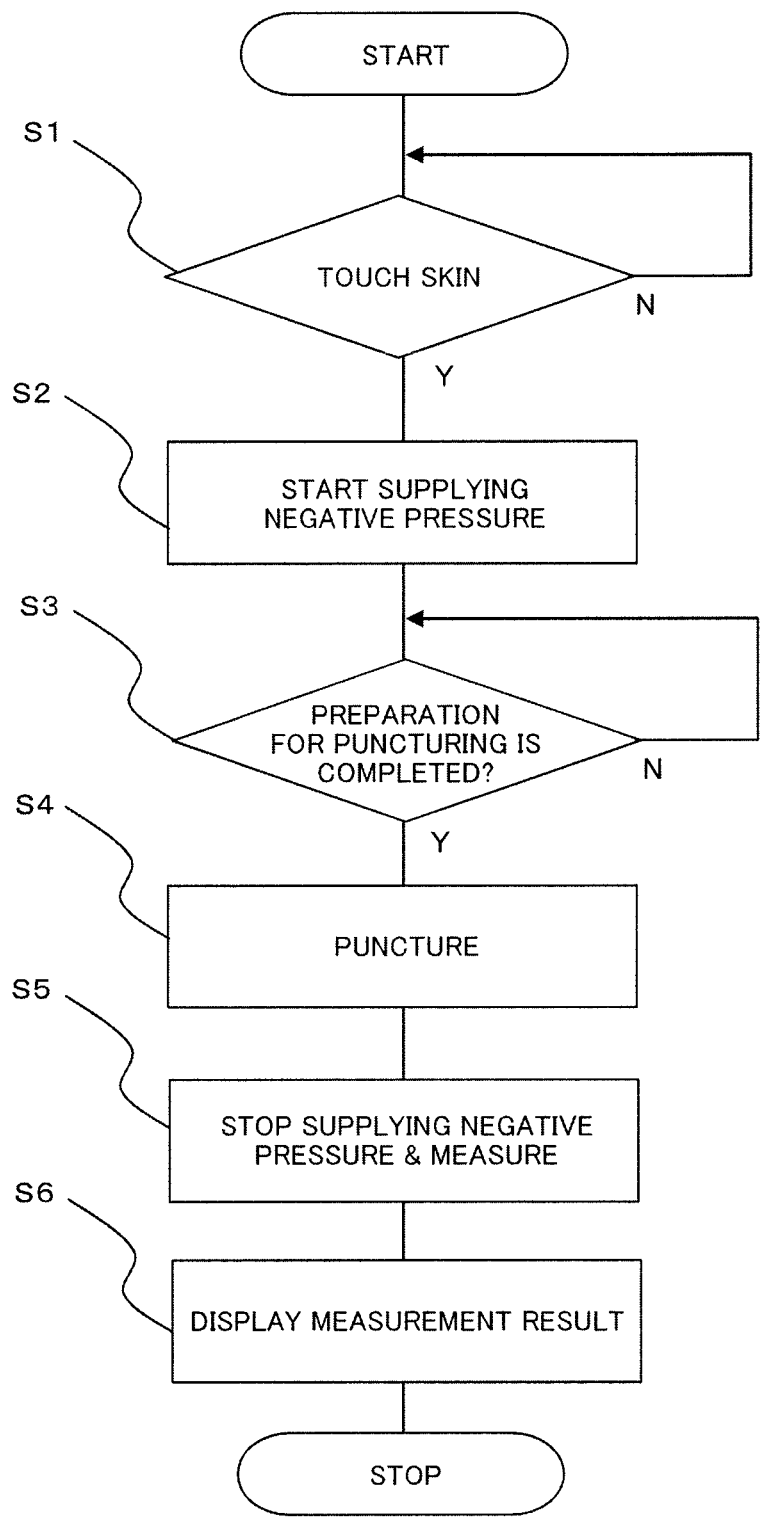
FIG. 11 is a flowchart of a blood analysis by the blood analysis apparatus of the embodiment.

FIG. 11 is a flowchart explaining the operation of blood sampling and analysis in blood analysis apparatus 70.

First, blood analysis apparatus 70 waits until finger 20 (see FIG. 9) of the user touches laser light emitting opening 10 in casing under side 9 of casing 70a. Here, a method of detecting to touch finger 20 in blood analysis apparatus 70 may be as follows: a touch sensor that detects touch with finger 20 may be provided on laser light emitting opening 10; and the user inputs from input section 74 (see FIG. 8) and blood analysis apparatus 70 may detect this input. Those inputs from the touch sensor and input section 74 are outputted to suction pump 17 through main control section 78. Suction pump 17 drives according to a command from this main control section 78. At this time, main control section 78 measures the driving time of suction pump 17 using timer 78a. Here, the signal from input section 74 may be outputted directly to suction pump 17.

Here, blood analysis apparatus 70 detects whether an input is performed from input section 74 in step S1, and if input section 74 performs input, the step moves to step S2.

In step S2, if input section 74 performs input (or detects the touching with skin), suction pump 17 drives and a negative pressure operation starts. By this means, a negative pressure is created in a region below blood analysis device A through negative pressure path 18, and after a predetermined period of time has passed, finger 20 located in the puncturing position facing the under surface side of blood analysis device A swell upward in laser light emitting opening 10.

In the present embodiment, the predetermined period of time, which is the negative pressure operation time, is 3 seconds, and when the timer measures 3 seconds after the negative pressure operation is started, the preparation for puncturing is completed in step S3. In blood analysis apparatus 70 according to the present embodiment, the predetermined period of time, which is the negative pressure operation time is measured by timer 78a included in main control section 78.

That is, in step S3, main control section 78 measures the time having passed after suction pump 17 starts the negative pressure operation by timer 78a and judges whether the predetermined period of time has passed. If the predetermined period of time has passed, main control section 78 judges that finger 20 located in the puncturing position swells upward in laser light emitting opening 10 and the step moves to step S4. Here, in step S3, timer 78a measures until the predetermined period of time has passed.

In step S4, main control section 78 makes laser unit 13 emit laser light. That is, main control section 78 commands laser unit section 13 to emit laser light and performs puncturing.

The laser light is focused by focusing lens 14 and passes through cover member 3 of blood analysis device A, one end 6a (through-hole 62) of passage 6 of spacer member 2 and blood collecting entrance 4 of base member 1, in order, and consequently the finger 20 is illuminated with laser light. By this means, part of the skin of finger 20 evaporates and blood 20a flows out from finger 20 to blood collecting entrance 4 of base member 1, and then moves, in passage 6 of spacer member 2, toward ventilation hole 5 located in the other end 6b by capillary action. By this means, blood 20a reaches blood analysis section 7.

In step S5, the supply of a negative pressure is stopped and blood analysis circuit section 72 analyzes, for example, the blood sugar level, the lactic acid level and the cholesterol level in blood analysis device 7. That is, in step S5, main control section 78 stops driving suction pump 17 and commands blood analysis circuit section 72 to analyze the blood, and the step moves to step S6.

In step S6, this result of analysis is displayed on display device 76 and a series of operations ends. That is, in step S6, blood analysis circuit section 72 outputs the result of analysis to display device 76 and makes display device 76 display that. Here, the result of analysis of blood analysis circuit section 72 may be outputted to display device 76 through main control section 78.

Blood analysis device A provides blood collecting entrance 4 and ventilation hole 5 only in the bottom part of device body 100, or, to be more specific, provides only on base member 1 forming the bottom part of device body 100, so that part of the blood does not spatter to the laser puncturing section 12 side, and laser puncturing section 12 is not stained with blood when the blood sampling and the analysis are performed.

In addition, in the present embodiment, cover member 3 forming the upper surface of blood analysis device A is optically transparent and covers the upper part of blood collecting entrance 4 that takes in blood 20a. By this means, a situation such that part of skin evaporated by irradiating laser light in the blood sampling enters blood collecting entrance 4 and reaches the laser puncturing section 12 side through through-hole 62 of spacer member 2, and then adheres on focusing lens 14 does not occur, so that the puncturing performance is not degraded and the inside of the blood analysis apparatus is not stained.

That is, in a case where the surface of skin is illuminated with laser light through blood analysis device A and part of the skin is evaporated and therefore blood 20a exudes on the surface of skin in the blood sampling, cover member 3 of blood analysis device A located above the light path of laser light can prevent evaporated materials of the part of the skin from reaching the laser puncturing section 12 side even if the part of skin is evaporated.

That is, there is no hole on the upper surface of blood analysis device A, blood does not adhere on the upper surface of blood analysis device A. By this means, blood is prevented from flowing into blood analysis apparatus 70 in which blood analysis device A is mounted.

Therefore, the evaporated materials of the part of the skin in the puncturing with laser light are prevented from entering the laser puncturing section 12 side, so that the laser puncturing section 12 side can be prevented from being stained.

In addition, when a negative pressure is applied to the skin to be punctured by suction pump 17, blood collecting entrance 4, which is the leading part of the capillary and ventilation hole 5 are formed in the same plane, so that a configuration in which blood collecting entrance 4 and ventilation hole 5 are located in different spaces is not provided, and therefore the difference of atmospheric pressure does not occur. By this means, blood flowing in the passage (capillary) moves in the passage (capillary) 6 only by capillary action, so that the blood does not flow backward in passage (capillary) 6 or does not burst out from the ventilation hole.

In addition, blood analysis device A mounted in blood analysis apparatus 70 is replaced every time the measurement is performed, so that the laser light path is not stained with components of skin. Therefore, skin is appropriately illuminated with laser light every time blood is sampled, so that appropriate blood sampling can be performed.

In addition, since the replacement of blood analysis device A performed with each cycle of the measurement can serve as the work to prevent the laser light path from being stained with evaporated skin components in the puncturing with laser light, it is not necessary to work to prevent the laser light path from being stained and it is convenient for the user.

According to blood analysis device A of the present embodiment as described above, when blood 20a is taken in blood analysis section 7 through blood collecting entrance 4, the blood does not adhere on any regions other than the under surface even if blood 20a flows from blood collecting entrance 4 to ventilation hole 5. By this means, the portion to be stained with blood 20a in used blood analysis device A can be localized, and the holding area which is not stained with blood can be increased, (i.e. widened) when blood analysis device A is held by blood analysis apparatus 70 having a puncturing apparatus that punctures skin and takes in blood from the punctured skin, and therefore the degree of freedom of use can be increased.

Here, although blood analysis device A according to the present embodiment does not have a hole penetrating blood analysis device A, as for the configuration of the blood analysis system included in blood test apparatus 70, a through-hole may be provided in a portion where blood analysis device A is not stained with blood.

The disclosure of Japanese Patent Application No. 2007-228530, filed on Sep. 4, 2007, including the specification, drawings and abstract, is incorporated herein by reference in its entirety.

The blood analysis device and the blood analysis apparatus according to the present invention bring about an effect that when blood is taken in the blood analysis section through the blood collecting entrance, any regions of the apparatus other than one surface are not stained with blood even if blood flows from the blood collecting entrance to the ventilation hole, increases the degree of freedom of use and is useful for the blood analysis apparatus having laser puncturing function.

The invention claimed is:

1. A blood analysis apparatus comprising:
a casing having a puncturing opening, the casing mounted internally of the blood analysis apparatus with a blood analysis device;
the blood analysis device comprises a device body having a first plate, a second plate and a third plate which are stacked in this order in a stacking direction,
the first plate has a blood collecting hole that receives blood and a ventilation hole, which are spaced apart from each other on a same plane and which penetrate the first plate in the stacking direction,
the second plate has an opening comprising a passage that communicates with the blood collecting hole and the ventilation hole, and a blood analyzer provided in the passage, the blood analyzer analyzing the blood received through the blood collecting hole, and
the third plate has an optically transmissive portion which is aligned with the blood collecting hole and through which laser light is passed to puncture a skin arranged in the blood collecting hole, the third plate having no hole communicating with the passage,
the casing is configured to have the blood analysis device mounted in the casing such that the blood collecting hole is aligned with the puncturing opening of the casing, and such that the first plate faces the skin and the third plate faces the puncturing section of the blood analysis apparatus, and
a puncturing section configured to puncture the skin with laser light, the puncturing section mounted in the casing such that the laser light of the puncturing section is aligned with the puncturing opening and blood collecting hole such that the laser light punctures the skin.

2. The blood analysis apparatus according to claim 1, further comprising a negative pressure creator that creates a negative pressure in the blood collecting hole of the blood analysis device that is mounted internally within the casing.

3. The blood analysis apparatus according to claim 1, said optically transmissive portion extends in a plane parallel to a plane of the first plate.

4. The blood analysis apparatus according to claim 1, said optically transmissive portion extends in a plane substantially perpendicular to the stacking order of said first, second and third plate.

* * * * *